United States Patent [19]

Cohnen et al.

[11] Patent Number: 4,810,712
[45] Date of Patent: Mar. 7, 1989

[54] BICYCLIC LACTAMS, PROCESSES FOR THEIR USE, AND FORMULATIONS CONTAINING THESE COMPOUNDS

[75] Inventors: Erich Cohnen, Jork; Petra Jacobitz, Hamburg, both of Fed. Rep. of Germany

[73] Assignee: Beiersdorf AG, Hamburg, Fed. Rep. of Germany

[21] Appl. No.: 139,000

[22] Filed: Dec. 29, 1987

Related U.S. Application Data

[63] Continuation of Ser. No. 776,948, Sep. 17, 1985, abandoned.

[30] Foreign Application Priority Data

Sep. 19, 1984 [DE] Fed. Rep. of Germany ....... 3434271

[51] Int. Cl.⁴ .................... C07D 215/22; A61K 31/47
[52] U.S. Cl. .................... 514/312; 514/213; 540/523; 546/157; 546/158
[58] Field of Search ................. 546/157, 158; 514/312

[56] References Cited

U.S. PATENT DOCUMENTS

| | | | |
|---|---|---|---|
| 3,975,391 | 8/1976 | Nakagawa et al. | 546/158 |
| 4,234,585 | 11/1980 | Winter et al. | 544/363 X |
| 4,340,595 | 7/1982 | Franke et al. | 540/523 X |
| 4,348,398 | 9/1982 | Atkinson et al. | 546/155 X |
| 4,581,367 | 4/1986 | Schromm et al. | 514/394 |
| 4,619,932 | 10/1986 | Banno et al. | 514/253 |

FOREIGN PATENT DOCUMENTS

| | | |
|---|---|---|
| 0011747 | 6/1980 | European Pat. Off. . |
| 1620124 | 3/1970 | Fed. Rep. of Germany . |
| 3131146 | 2/1983 | Fed. Rep. of Germany . |
| 0016478 | 2/1979 | Japan ................. 546/158 |
| 2070588 | 9/1981 | United Kingdom . |

OTHER PUBLICATIONS

Yo et al, Chemical Abstracts, vol. 95, 203705t (1981).
Nakao et al., Chemical Abstracts, vol. 94, 65712u (1981).
Tominaga et al, Chemical Abstracts, vol. 90, 87304g (1979).
Houben-Weyl, Thieme-Verlag: Meth. der Org. Chemie, Stuttgart (1981), p. 750.
Beyer, Hirzel Verlag: Lehrbuch der Org. Chemie, Stuttgart (1981), pp. 190, 203.
Nakagawa et al., Chemical Abstracts, vol. 86, 189738m (1977).
Nakagawa et al., Chemical Abstracts, vol. 87, 53098r (1977).
Nishi et al., Chemical Abstracts, vol. 88, 62307f (1978).
Chemical Abstracts, Chem. Substance Index, vol. 87 (1977), p. 5037CS.

Primary Examiner—Donald G. Daus
Assistant Examiner—Diana G. Rivers
Attorney, Agent, or Firm—Sprung Horn Kramer & Woods

[57] ABSTRACT

Bicyclic lactams of the general formula I

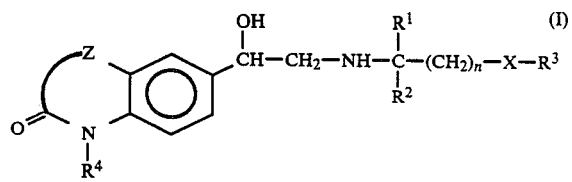

in which $R^1$ and $R^2$, which can be identical or different, denote a hydrogen atom or an alkyl group with 1 to 3 carbon atoms, $R^3$ denotes an unsubstituted phenyl group or a phenyl group which is substituted by a halogen atom, one or two alkoxy groups, a methylenedioxo group or one or several hydroxyl groups, or denotes a pyridyl group, an indolyl group, a 1,2-benzisoxazolyl group which is optionally substituted by a halogen atom or the benzimidazol-2-one or 1,4-benzodioxane radical, $R^4$ denotes a hydrogen atom or an alkyl group with 1 to 6 carbon atoms or a carbalkoxymethylen group, Z denotes a straight-chain, saturated or unsaturated alkylene group with 2 or 3 carbon atoms, which is optionally alkylated, X denotes an oxygen atom or a single bond and n denotes the number 1, 2 or 3, and their tautomeric forms and their salts and acid addition salts, block both the alpha and the beta receptors of the adrenergic system and are therefore suitable for the treatment of hypertension, circulatory disturbances, angina pectoris and coronary insufficiency.

11 Claims, No Drawings

BICYCLIC LACTAMS, PROCESSES FOR THEIR USE, AND FORMULATIONS CONTAINING THESE COMPOUNDS

This a continuation of application Ser. No. 776,948, filed Sept. 17, 1985, now abandoned.

The invention relates to new bicyclic lactams of the genral formula I

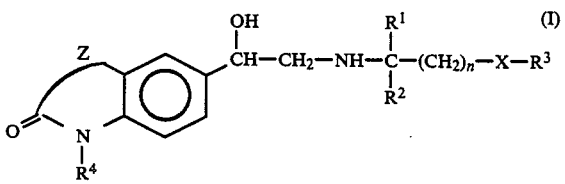

in which $R^1$ and $R^2$, which can be identical or different, denote a hydrogen atom or an alkyl group with 1 to 3 carbon atoms, $R^3$ denotes an unsubstituted phenyl group or a phenyl group which is substituted by a halogen atom, one or two alkoxy groups, a methylenedioxo group or one or several hydroxyl groups, or denotes a pyridyl group, an idolyl group, a 1,2-benzisoxazolyl group which is optionally substituted by a halogen atom or the benzimidazol-2-one or 1,4-benzodioxane radical, $R^4$ denotes a hydrogen atom or an alkyl group with 1 to 6 carbon atoms or a carbalkoxymethylen group, Z denotes a straight chain, saturated or unsaturated alkylene group with 2 or 3 carbon atoms, which is optionally alkylated, X denotes an oxygen atom or a single bond and n denotes the number 1, 2 or 3, and their tautomeric forms and their salts and acid addition salts, processes for their preparation and their use, and formulations containing these compounds.

Some compounds of the formula I are described in the literature: Japanese Preliminary Published Specification No. 76,125,291 (Otsuka Pharm. Co.) and Chem. Abstr. 87:53 098r. These are the compounds 6-(2-benzylamino-1-hydroxy)ethyl-3,4-dihydrocarbostyril and 6-(2-methylbenzylamino- 1-hydroxy)ethyl-3,4-dihydroxycarbostyril.

For simplicity, the compounds according to the invention are defined in only one of the tautomeric forms represented by formula I. However, the invention extends to all the tautomeric forms of the compounds.

Although pharmaceutically acceptable salts and acid addition salts of the new compounds of the formula I and the tautomeric forms thereof are preferred, all the salts lie within the scope of the invention. All the salts are useful for the preparation of the compounds, even if the specific salt is desired only as an intermediate, such as, for example, if the salt is formed only for the purpose of purification or identification, or if it is used as an intermediate product in the preparation of a pharmaceutically acceptable salt, for example by ion exchange procedures.

The compounds of the general formula I and salts thereof contain asymmetric carbon atoms. The present invention therefore also relates to the various optical isomers and the diastereoisomers, as well as the salts and addition salts of these compounds with acids. The racemates can be resolved into their optical antipodes by methods which are known per se.

The alkyl groups according to the invention and the alkyl components of the alkoxy groups can be straight-chain or branched and are preferably methyl, ethyl and propyl groups.

Halogen is fluorine, chlorine, bromine or iodine, preferably fluorine, chlorine or bromine, and in particular chlorine.

The radical $R^1$ is preferably hydrogen, methyl or ethyl. The radicals $R^1$ and $R^2$ are furthermore preferably identical and denote hydrogen or straight-chain alkyl groups, in particular methyl and ethyl groups. Mixed alkyl substituents $R^1$ and $R^2$, in particular methyl and ethyl, are also preferred.

Preferred substituents $R^3$ are unsubstituted phenyl groups or phenyl groups which are substituted as described, phenyl being preferred. Hydroxy phenyl groups preferably carry one or two hydroxy groups.

$R^4$ is preferably hydrogen or an alkyl group with up to three carbon atoms, in particular methyl or ethyl. The carbalkoxymethylen groups contain 1 to 6 carbon atoms and preferably 1 to 3 carbon atoms in the alkoxy radical. Particularly preferred alkoxy groups are methoxy or ethoxy groups.

The unsaturated alkylene group Z preferably contains one olefinic double bond. Alkylated alkylene groups Z have one to three, preferably one, straight-chain or branched alkyl group with 1 to 4 carbon atoms, in particular methyl and/or ethyl groups.

Preferred alkylene groups Z are:

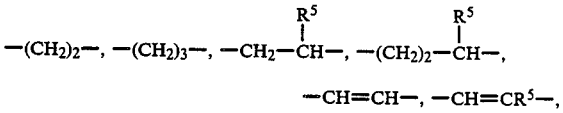

$$-CH=CH-, -CH=CR^5-,$$

wherein $R^5$ denotes an alkyl group with 1 to 4 carbon atoms, in particular methyl and ethyl. $R^5$ is preferably in the 4- or 5-position of the bicyclus. Preferred are saturated alkylene groups Z.

The 3,4-dihydro-quinolin-2-one compounds where Z denotes $-(CH_2)_2-$ or $-CH_2-CR^5H-$ are particularly preferred.

X is preferably a single bond and n preferably denotes the number 2.

Compounds which preferably contain at least 2 or 4, in particular at least 5 and particularly preferably exactly 5, carbon atoms in the alkyl group formed by $-CR^1R^2-(CH_2)_n-$ in the formula I are furthermore preferred. In these cases, n is preferably 2. These compounds are then furthermore particularly preferred if $R^3$ denotes phenyl or substituted phenyl, as described, phenyl being preferred.

Particularly preferred compounds of the formula I according to the invention are those 3,4-dihydroquinolinones ($Z=-(CH_2)_2-$) in which $R^1$ and $R^2$ are each methyl, n is 2 or 3, in particular 2, X is a single bond and $R^3$ is phenyl or phenyl which is substituted as described, phenyl being preferred.

1,2-Benzisoxazole groups $R^3$ can carry a halogen atom or can be unsubstituted and are preferred radicals $R^3$.

If X denotes a single bond, $R^3$ is bonded to the $-(CH_2)_n-$ group.

Furthermore, benzazepin compounds with $Z=-(CH_2)_3-$ and $-(CH_2)_2-CHR^5-$ are preferred.

The following compounds according to the invention and salts and acid addition salts thereof with a high therapeutic effect are particularly preferred, and in particular in the form of the racemates and in the form of optically active isomers: 3,4-dihydro-6-[1-hydroxy-2-[(1-methyl-3-phenyl-propyl)-amino]-ethyl]-quinoline-2-(1H)-one, 3,4-dihydro-6-[1-hydroxy-2-[[1-methyl-2-(2-methoxy-phenoxy)-ethyl]-amino]ethyl]-quinolin-2(1H)-one, 3,4-dihydro-6-[1-hydroxy-2-[[1-methyl-3-(6-(6-chloro-1,2-benzisoxazol-3-yl)-propyl]-amino]-ethyl]-quinolin-2-(1H)-one, 3,4-dihydro-6-[1-hydroxy-2-[[1,1-dimethyl-3-(2-methoxy-phenyl)-propyl]-amino]-ethyl]-quinolin-2-(1H)-one, 3,4-dihydro-6-[1-hydroxy-2-[(1,1-dimethyl-3-phenyl-propyl)-amino]-ethyl]-quinolin-2-(1H)-one, 6-[1-hydroxy-2-[[1,1-dimethyl-3-(2-methoxyphenyl)-propyl]-amino]-ethyl]-quinolin-2-(1H)-one and 7-[1-hydroxy-2-[(1,1-dimethyl-3-phenyl-propyl)-amino]-ethyl]-1,3,4,5-tetrahydro-2H-1-benzazepin-2-one.

Of these compounds, 3,4-dihydro-6-[1-hydroxy-2-[(1,1-dimethyl-3-phenyl-propyl)-amino]-ethyl]-quinolin-2(1H)-one is particularly preferred. It is distinguished by a particularly high potent action.

The compounds of the formula I according to the invention and their isomers and their physiologically acceptable salts and acid addition salts are therapeutic active compounds, have a powerful pharmacological action and are useful medicaments. They block both the alpha receptors and the beta receptors of the adrenergic system and are therefore preferably suitable for the treatment of hypertension, circulatory disturbances, in particular peripheral circulatory disturbances, angina pectoris and coronary insufficiency.

Combination of an alpha receptor-blocking property with a beta receptor-blocking property is expedient for two reasons:

1. In contrast to a beta-blockade along, the increased blood pressure is predominantly reduced by the reduction in peripheral vascular resistance transmitted via alpha receptors; a reflectory increase in cardiac output is prevented by the beta receptor-blocking property of the substances.

2. Activation of the renin/angiotensin system which is observed after vasodilation by alpha-blockade and has a blood pressure-increasing influence is suppressed by beta-blockade.

When administered to rabbits perorally in a dose of 10 to 100 mg/kg, the compounds mentioned in the present invention reduce the isoprenaline-induced tachycardia by 50% (beta$_1$-blockade) and the phenylephrine-induced increase in blood pressure by 50% (alpha$_1$-blockade).

The compounds of the present invention can be administered orally or parenterally. The individual dose for humans is 1 mg to 500 mg, preferably 10 mg to 100 mg and in particular 30 mg to 50 mg. These dosages are advantageous for the treatment of the abovementioned diseases, in particular for the treatment of hypertension.

As is customary for alpha and beta receptors, the daily dose is to be adapted to suit the individual, because it depends on the receptor sensitivity and the sympathetic tone of the patient. The treatment is advantageously started at low doses and then increased.

According to the invention, pharmaceutical compositions which contain a compound of the formula I or pharmaceutically acceptable salts thereof together with a pharmaceutically acceptable diluent or excipient are provided.

The compounds according to the invention can be mixed with customary pharmaceutically acceptable diluents or excipients and, if appropriate, with other auxiliaries and administered, for example, orally or parenterally. They can be administered orally in the form of tablets, coated tablets, syrups, suspensions and liquids or parenterally in the form of solutions or suspensions. Products which are to be administered orally can contain one or more additives, such as sweetners, aromatising agents, dyestuffs and preservatives. Tablets can contain the active compound mixed with customary pharmaceutically acceptable auxiliaries, for example inert diluents, such as calcium carbonate, sodium carbonate, lactose and talc, granulating agents and agents which promote the disintegration of the tablets on oral administration, such as starch or alginic acid, binders, such as starch or gelatine, and lubricants, such as magnesium stearate, stearic acid and talc.

Examples of suitable excipients are milk sugar (lactose), gelatine, maize starch, stearic acid, ethanol, propylene glycol, ethers of tetrahydrofuryl alcohol and water.

The tablets can be coated by known procedures, in order to delay disintegration and absorption in the gastrointestinal tract, which means that the activity of the active compound can extend over a longer period of time. In the suspensions, the active compound can likewise be mixed with auxiliaries which are customary for the preparation of such compositions, for example suspending agents, such as methylcellulose, tragacanth or sodium alginate, wetting agents, such as lecithin, polyethylene stearate and polyoxyethylene sorbitan monooleat, and preservatives, such as ethyl parahydroxybenzoate. Capsules can contain the active compound as the sole constituent or mixed with a solid diluent, such as calcium carbonate, calcium phosphate or kaolin. The injectable products are likewise formulated in a manner which is known per se. The pharmaceutical products can contain the active compound in an amount of 0.1 to 90%, in particular 1 to 90%, the remainder being an excipient or additive. In view of preparation and administration, solid products, such as tablets and capsules, are preferred. The products preferably contain the active compound in an amount of 10 to 50 mg.

A first process for the preparation of the compounds of the formula I is characterised in that halogenoketones of the general formula II

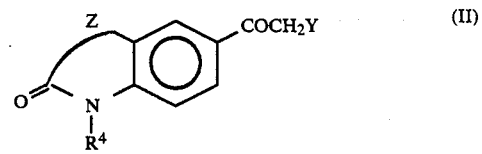
(II)

in which $R^4$ and Z have the meaning given and Y denotes a chlorine or bromine atom, are reacted with an amine $R^6R^7$—NH, in which $R^6$ denotes a hydrogen atom or a benzyl group and $R^7$ denotes the group

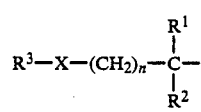

wherein $R^1$, $R^2$, $R^3$, X and n are as defined above, to give the aminoketones of the general formula III:

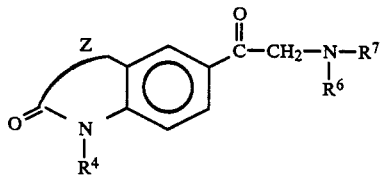

(III)

Compounds of the formula III in which $R^6$ represents a benzyl group are converted into the compounds according to the invention by catalytic hydrogenation, and compounds of the formula III in which $R^6$ denotes a hydrogen atom are converted into compounds of the formula I by reduction of the keto group with complex metal hydrides or catalytic hydrogenation.

The reaction of the halogenoketones with amines is carried out in a suitable solvent, such as dimethylformamide, acetonitrile or tert.-butanol, in the presence of a tertiary amine, such as triethylamine or pyridine, or an acid-binding agent, such as, for example, sodium carbonate.

The reduction of the ketone of the formula (III) is carried out in an alcohol, such as methanol or ethanol, with complex metal hydrides, such as sodium borohydride, or by catalytic reduction with hydrogen in the presence of noble metal catalysts, such as platinum, palladium or Raney nickel. Any benzyl protective group ($R^6=CH_2C_6H_5$) present is split off hydrogenolytically in teh catalytic reduction.

Another process for the preparation of the compounds of the formula I is characterised in that an aminoalcohol of the formula IV

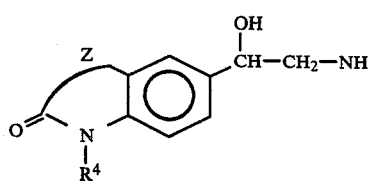

(IV)

with the meaning given for $R^4$ and Z, which can be obtained by reaction of a halogenoketone of the formula II with dibenzylamine and subsequent catalytic hydrogenation, is subjected to a condensation reaction with a suitable aldehyde or ketone of the general formula V

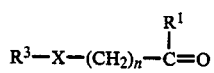

(V)

in which $R^1$, $R^3$, X and n have the meaning given, and the azomethine intermediately formed is converted into the compounds of the formula I according to the invention with a complex metal hydride or by catalytic reduction with hydrogen.

The condensation of the amine of the formula (IV) with a ketone or aldehyde (V) is carried out in suitable solvents, such as alcohols, at temperatures of 20°-100° C. The reduction of the azomethine is carried out in the same solvent by complex metal hydrides, preferably sodium borohydride, or catalytic reduction with hydrogen and catalysts such as Raney nickel, palladium or platinum, at room temperature.

Another process for the preparation of the compounds of the formula I is characterised in that an alpha-ketoaldehyde of the formula VI

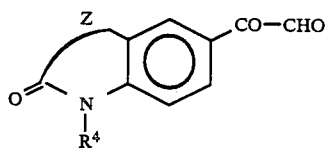

(VI)

in which $R^4$ and Z have the meaning given, is reacted with an amine of the formula VII

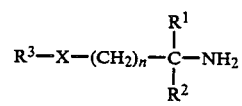

(VII)

in which $R^1$, $R^2$, $R^3$, X and n have the meaning given, and the resulting azomethine intermediate is reduced with complex metal hydrides or by a catalytic route with hydrogen and in this manner is converted into the compounds of the formula I according to the invention.

The condensation of the amine of the formula VII with a keto-aldehyde (VI) is carried out in suitable solvents, such as alcohols, at temperatures of 20°-100° C. The reduction of the azomethine is carried out in the same solvent by complex metal hydrides, preferably sodium borohydride, or catalytic reduction with hydrogen and catalysts such as Raney nickel, palladium or platinum, at room temperature.

The starting compounds are known or can be obtained by known processes.

The compounds of the general formula I can be either bases or acids or amphoteric and can therefore be isolated from the reaction mixtures in the form of their salts or acid addition salts. As bases, they can be converted into salts with suitable inorganic or organic acids by known processes, or as acids they form salts with bases.

Physiologically acceptable salts or acid addition salts are preferred. Examples of inorganic acids which are suitable for this purpose are hydrogen halide acids, for example hydrochloric acid, or sulphuric acid, and examples of suitable organic acids are fumaric acid, maleic acid, citric acid and tartaric acid. For the preparation, an alcoholic solution of a suitable acid is added to the hot alcoholic solution of the base to give, after addition of ether, the salt. Preferred salts are the alkali metal, alkaline earth metal and ammonium salts of the compounds of the formula I, which are obtained with the corresponding bases, in particular sodium hydroxide, potassium hydroxide or ammonium hydroxide.

Diastereoisomers can be separated into their racemic modifications in a known manner on the basis of the physicochemical differences of their constituents. Racemates can be resolved by known methods, for example by recrystallisation in optically active solvents, by microorganisms or by reaction with optically active acids or bases which form a salt with the racemic compound, separation of the diastereoisomers by fractional crystallisation and liberation of the enantiomers by suitable agents. Examples of particularly suitably optically active acids are the d- and l-forms of tartaric acid, ditoluyltartaric acid, malic acid, mandelic acid, camphorsulphonic acid or pyrrolidone-carboxylic acid. Suitably optically active bases are alpha-phenylethylamine, menthylamine, ephedrine, brucine and quinine. The more active of the antipodes is advantageously isolated. According to the invention, however, it is also possible to obtain the pure enantiomers by asymmetric synthesis.

The following examples serve to illustrate the invention:

EXAMPLE 1

3,4-Dihydro-6-[1-hydroxy-2-[(1,1-dimethyl-3-phenyl-propyl)-amino]-ethyl]-quinolin-2(1H)-one A solution of 1.4 g (0.006 mole) of 3,4-dihydro-6-(alpha,alpha-dihydroxy-acetyl)-quinolin-2-(1H)-one and 1.37 g (0.008 mole) of 1,1-dimethyl-3-phenyl-propanamine in 60 ml of ethanol and 30 ml of dimethylformamide is heated to 80° C. for 2 hours and, after cooling to room temperature, about 1.5 g of sodium borohydride are gradually added. After 2 hours, the mixture is acidified with acetic acid and the solvent is evaporated off in vacuo. After being rendered alkaline with 2N sodium hydroxide solution, the residue is extracted with methylene chloride. The residue of the organic phase is purified by column chromatography on silica gel (CHCl$_3$/MeOH 93/7).

1.25 g of 3,4-dihydro-6-[1-hydroxy-2-[1,1-dimethyl-3-phenyl-propyl)-amino]-ethyl]-quinoline-2-(1H)-one hydrochloride are obtained with ethanolic hydrochloric acid after recrystallisation from isopropanol. Melting point 231°–232° C. (decomposition).

The following compounds of the formula I (X=— denotes a single bond), wherein R$^4$ and R$^5$ are hydrogen and Z denotes —(CH$_2$)$_2$— (3,4-dihydro-quinolin-2-one compounds) were prepared analogously to Example 1:

| EXAMPLE | R$^1$ | R$^2$ | R$^3$ | X | n | SALT | MELTING POINT °C. |
|---|---|---|---|---|---|---|---|
| 2 | CH$_3$ | CH$_3$ | 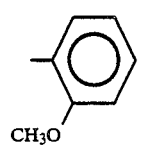 | — | 2 | Fumarate Hydrochloride | 207–209 182(decomposition) |
| 3 | CH$_3$ | CH$_3$ | 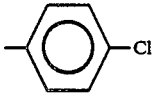 | — | 2 | Hydrochloride | 180(decomposition) |
| 4 | CH$_3$ | CH$_3$ | 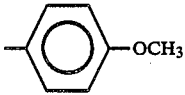 | — | 2 | Hydrochloride | 238(decomposition) |
| 5 | CH$_3$ | CH$_3$ | 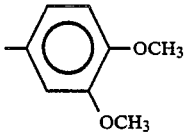 | — | 2 | | |
| 6 | CH$_3$ | CH$_3$ | 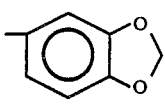 | — | 2 | | |
| 7 | CH$_3$ | CH$_3$ | 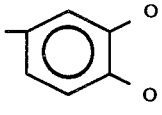 | — | 2 | Hydrochloride | 195 |
| 8 | CH$_3$ | CH$_3$ | 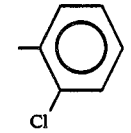 | — | 2 | | |
| 9 | CH$_3$ | CH$_3$ | 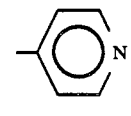 | — | 2 | Dihydrochloride | 204(decomposition) |
| 10 | CH$_3$ | CH$_3$ | 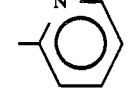 | — | 2 | Dihydrochloride | 195–196(decomposition) |

-continued

| EXAMPLE | R¹ | R² | R³ | X | n | SALT | MELTING POINT °C. |
|---|---|---|---|---|---|---|---|
| 11 | $CH_3$ | $CH_3$ | 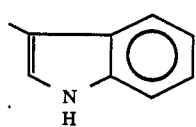 | — | 1 | Hydrochloride | 254–256 |
| 12 | $CH_3$ | $CH_3$ | 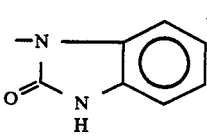 | — | 3 | Hydrochloride | amorphous |
| 13 | $CH_3$ | $CH_3$ | 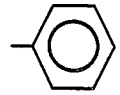 | — | 3 | Base | 170° |

The following examples provide with $R^5$ also the position of this substituent of the bicyclus together with the corresponding Z with this substituent $R^5$.

| EXAMPLE | R¹ | R² | R³ | R⁴ | R⁵ | X | Z | n | SALT | MELTING POINT °C. |
|---|---|---|---|---|---|---|---|---|---|---|
| 14 | $CH_3$ | $CH_3$ | 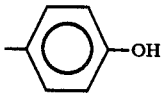 | H | H | — | $(CH_2)_2$ | 2 | HCl | 219 |
| 15 | $CH_3$ | $CH_3$ |  | H | 4-$CH_3$ | — | $-CH_2-\overset{CH_3}{\underset{\|}{CH}}-$ | 2 | HCl | 212 |
| 16 | $CH_3$ | $CH_3$ | 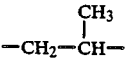 | $CH_3$ | H | — | $(CH_2)_2$ | 2 | HCl | 227 |
| 17 | $CH_3$ | $CH_3$ |  | H | H | — | $(CH_2)_3$ | 2 | HCl | 210 |
| 18 | $CH_3$ | $CH_3$ | 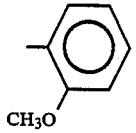 | H | H | — | $(CH_2)_2$ | 2 | HCl | amorphous |
| 19 | $CH_3$ | $CH_3$ | 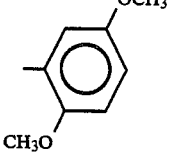 | H | H | — | $(CH_2)_2$ | 3 | HCl | 156 |
| 20 | $CH_3$ | $CH_3$ | 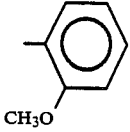 | H | H | — | $(CH_2)_2$ | 2 | HCl | amorphous |

| EXAMPLE | R¹ | R² | R³ | R⁴ | R⁵ | X | Z | n | SALT | MELTING POINT °C. |
|---|---|---|---|---|---|---|---|---|---|---|
| 21 | $CH_3$ | $CH_3$ | (phenyl with $CH_3O$) | H | H | — | —CH=CH— | 2 | | |
| 22 | $CH_3$ | $CH_3$ | (phenyl) | $CH_2COOCH_3$ | H | — | $(CH_2)_2$ | 2 | HCl | 230 |
| 23 | $CH_3$ | $CH_3$ | (phenyl with OH, OH) | H | H | — | $(CH_2)_2$ | 2 | | |

EXAMPLE 24

3,4-Dihydro-6-[1-hydroxy-2-[[1-methyl-3-(1,3-benzodioxol-5-yl)-propyl]-amino]-ethyl]-quinolin-2(1H)-one A suspension of 3.0 g (0.012 mole) of 3,4-dihydro-6-(2-amino-1-hydroxyethyl)-quinolin-2(1H)-one hydrochloride in ethanol is neutralised with sodium ethylate solution (0.013 mole) and, after addition of 4.60 g (0.024 mole) of 4-(1,3-benzodioxol-5-yl)-butan-2-one, the mixture is heated at the boiling point for 2 hours. After cooling, 2.3 g of sodium borohydride are added in portions and the mixture is then stirred at room temperature for one hour and acidified with acetic acid. The solvent is removed in vacuo and 2N sodium hydroxide solution is added to the residue. The mixture is extracted with methylene chloride, the organic phase is evaporated and the residue is converted into the hydrochloride of 3,4-dihydro-6-[1-hydroxy-2-[[1-methyl-3-(1,3-benzodioxol-5-yl)-propyl]-amino]-ethyl]-quinolin-2(1H)-one with ethanolic hydrochloric acid.

Recrysallisation from isopropanol gives 1.2 g of melting point 187°–190° C. (decomposition).

The same compound is also obtained by catalytic hydrogenation, by means of hydrogen at room temperature and 10 bar in the presence of palladium-on-charcoal (10%), of the azomethine intermediately formed from the amine and ketone.

The folowing compounds of the formula I (X=— denotes a single bond) wherein R⁴ and R⁵ are hydrogen and Z denotes —$(CH_2)_2$— (3,4-dihydro-quinolin-2-one compounds) are synthesised analogously to Example 24:

| EXAMPLE | R¹ | R² | R³ | X | n | SALT | MELTING POINT °C. |
|---|---|---|---|---|---|---|---|
| 25 | H | $CH_3$ | (phenyl) | — | 2 | Hydrochloride | 169–171(decomposition) |
| 26 | H | $CH_3$ | (phenyl with $CH_3O$) | 0 | 1 | Hydrochloride | 158–159(decomposition) |
| 27 | H | $CH_3$ | (phenyl with $OCH_3$) | — | 1 | Hydrochloride | 174 |
| 28 | H | H | (phenyl with $CH_3O$) | 0 | 1 | Hydrochloride | 156–158(decomposition) |
| 29 | H | $CH_3$ | (benzodioxole) | — | 2 | | |

-continued

| EXAMPLE | R¹ | R² | R³ | X | n | SALT | MELTING POINT °C. |
|---|---|---|---|---|---|---|---|
| 30 | H | CH₃ | ![4-methoxy-2-methylphenyl] | — | 2 | Hydrochloride | 209(decomposition) |
| 31 | H | CH₃ | ![5-chloro-benzisoxazol-3-yl] | — | 2 | Hydrochloride | 197–198(decomposition) |
| 32 | H | CH₃ | ![3-methoxy-2-methylphenyl] | — | 2 | Hydrochloride | 178–180(decomposition) |

EXAMPLE 33

3,4-Dihydro-6-[1-hydroxy-2-[[1,1-dimethyl-3-(2-methoxy-phenyl)-propyl]-amino]-ethyl]-quinolin-2-(1H)-one 6.0 g (0.023 mole) of 3,4-dihydro-6-bromoacetyl-quinolin-2(1H)-one, 4.8 g (0.025 mole) of 1,1-dimethyl-3-(2-methoxy-phenyl)-propanamine and 3.2 g (0.03 mole) of potassium carbonate are stirred in 100 ml of dimethylformamide at room temperature for 24 hours. After dilution with methanol, the product is reduced with an excess of sodium borohydride. The solvents are removed in vacuo, the residue is taken up in methylene chloride and the mixture is extracted with water. Column chromatography on silica gel (CHCl₃/MeOH 90/10) gives 3,4-dihydro-6-[1-hydroxy-2-[[1,1-dimethyl-3-(2-methoxy-phenyl)-propyl]-amino]-ethyl]-quinolin-2(1H)-one as a base, which is converted into the hydrochloride in the customary manner. Melting point 180° C. (decomposition).

EXAMPLE 34

Preparation of tablets

Tablets which contain the constituents shown below are prepared by known procedures. These are suitable for the treatment of the abovementioned diseases, in particular hypertension, in a dosage amount of 40 mg once or twice daily.

|  | Tablet A | Tablet B |
|---|---|---|
| 3,4-Dihydro-6-[1-hydroxy-2-[[1-methyl-2-(2-methoxy-phenoxy)-ethyl]-amino]-ethyl]-quinolin-2(1H)—one hydrochloride | 40 mg | 20 mg |
| Lactose | 90 mg | 90 mg |
| Maize starch | 5 mg | 5 mg |
| magnesium stearate | 1 mg | 1 mg |

EXAMPLE 35

Preparation of ampoules

Ampoules containing the constituents mentioned below can be prepared in a known manner. The active compound and sodium chloride are dissolved in water and glass ampoules are filled with the solution, under nitrogen.

| 3,4-Dihydro-6-[1-hydroxy-2-[(1-methyl-3-phenyl-propyl)-amino]-ethyl]-quinolin-2(1H)—one hydrochloride | 10 mg |
|---|---|
| Sodium chloride | 18 mg |
| distilled water to | 2.0 ml |

EXAMPLE 36

Preparation of tablets

Tablets which contain the constituents shown below are prepared by known procedures. These are suitable for the treatment of the abovementioned diseases, in particular hypertension, in a dosage amount of 30 mg once or twice daily.

|  | Tablet A | Tablet B |
|---|---|---|
| 3,4-Dihydro-6-[1-hydroxy-2-[(1,1-dimethyl-3-phenyl-propyl)-amino]-ethyl]-quinolin-2(1H)—one | 30 mg | 10 mg |
| Lactose | 90 mg | 90 mg |
| Maize starch | 5 mg | 5 mg |
| Magnesium stearate | 1 mg | 1 mg |

We claim:
1. A bicyclic lactam of the formula

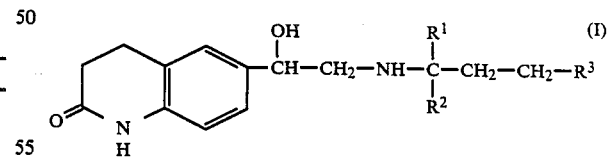

in which

R¹ and R², which can be identical or different each is an alkyl group with 1 to 3 carbon atoms, and R³ is an unsubstituted phenyl group or a phenyl group which is substituted by a halogen atom, one or two alkoxy groups, a methylenedioxo group or one or two hydroxyl groups, or its tautomer, or an acid addition salt thereof.

2. A compound according to claim 1, wherein R¹ and R² are methyl.

3. A compound according to claim 1, wherein R³ is phenyl.

4. A compound according to claim 1, wherein such compound is 3,4-dihydro-6-(1-hydroxy-2-(1,1-dimethyl-3-phenyl-propyl)-amino)-ethyl)-quinolin-2-(1H)-one.

5. A compound of claim 1 which is 3,4-dihydro-6-(1-hydroxy-2-((1,1-dimethyl-3-(2-methoxyphenyl)-propyl)-amino)-ethyl)-quinolin-2-(1H)-one.

6. A pharmaceutical formulation for blocking alpha- and beta-receptors of the adrenergic system containing as an active ingredient an alpha- or beta-receptor blocking amount of a bicyclic lactam of claim 1 in admixture with an inert pharmaceutical carrier.

7. A composition according to claim 6, wherein such compound is 3,4-dihydro-6-(1-hydroxy-2-((1,1-dimethyl-3-phenyl-propyl)-amino)-ethyl)-quinolin-2-(1H)-one.

8. A composition according to claim 6 which is 3,4-dihydro-6-(1-hydroxy-2-(1,1-dimethyl-3-(2-methoxy-phenyl)-propyl)-amino)-ethyl)-quinolin-2-(1H)-one.

9. A method of blocking alpha- and beta-receptors of the adrenergic system in warm blooded animals which comprises administering to the animals an effective amount of an alpha- or beta-blocking receptor of the adrenergic system according to claim 1 together with an inert pharmaceutical carrier.

10. The method according to claim 9, wherein such compound is 3,4-dihydro-6-(1-hydroxy-2-((1,1-dimethyl-3-phenyl-propyl)-amino)-ethyl)-quinolin-2-(1H)-one.

11. The method according to claim 9, wherein such compound is 3,4-dihydro-6-(1-hydroxy-2-(1,1-dimethyl-3-(2-methoxy-phenyl)-propyl)-amino)-ethyl)-quinolin-2-(1H)-one.

* * * * *

UNITED STATES PATENT AND TRADEMARK OFFICE
CERTIFICATE OF CORRECTION

PATENT NO. : 4,810,712

DATED : March 7, 1989

INVENTOR(S) : Erich Cohnen, et al

It is certified that error appears in the above-identified patent and that said Letters Patent is hereby corrected as shown below:

Col. 1, line 9, correct spelling of --general--.
Col. 3, line 4, insert -- - -- (hypen) after "amino".
Col. 3, line 5, end of line delete "(6-".
Col. 3, line 33, delete "along" and substitute --alone--.
Col. 5, line 31, delete "teh" and substitute --the--.
Col. 6, lines 65 and 68, delete "Suitably" and substitute --Suitable--.
Col. 15, line 2, "2-(1,1" should read --2-((1,1--.

Signed and Sealed this

Twenty-fourth Day of April, 1990

*Attest:*

HARRY F. MANBECK, JR.

*Attesting Officer*     *Commissioner of Patents and Trademarks*